United States Patent [19]

Zimmerman et al.

[11] 4,453,939

[45] Jun. 12, 1984

[54] COMPOSITION FOR SEALING AND HEALING WOUNDS

[75] Inventors: Eberhard Zimmerman, Munster; Ulrich Schiele, Munich, both of Fed. Rep. of Germany

[73] Assignee: Hormon-Chemie Munchen GmbH, Munich, Fed. Rep. of Germany

[21] Appl. No.: 347,817

[22] Filed: Feb. 11, 1982

[30] Foreign Application Priority Data

Feb. 16, 1981 [DE] Fed. Rep. of Germany ....... 3105624

[51] Int. Cl.³ .......................................... A61K 37/02
[52] U.S. Cl. .................................... 604/368; 604/304; 128/156
[58] Field of Search ................ 424/177; 128/155–156; 604/891, 896–897, 47, 285, 286, 288, 304–306, 356, 358, 364, 368

[56] References Cited

U.S. PATENT DOCUMENTS 4,265,233 5/1981 Sugitachi et al. .................. 128/156

FOREIGN PATENT DOCUMENTS 1205609 9/1970 United Kingdom .
2023614 10/1978 United Kingdom .
2041942 9/1980 United Kingdom .

OTHER PUBLICATIONS

Wiener Medizinische Wochenschrift 7, 86 to 89 (1976).

*Primary Examiner*—C. Fred Rosenbaum
*Assistant Examiner*—Sherri E. Vinyard
*Attorney, Agent, or Firm*—Mark Dryer

[57] ABSTRACT

A composition and its use for sealing and healing of wounds, comprising a collagen carrier which is coated on one face or all faces with a mixture of (1) a fibrinogen component which contains fibrinogen, factor XIII-containing fibrinogen or a mixture thereof, and (2) a thrombin component which contains thrombin, a substance which liberates thrombin in the presence of body fluid or a mixture of such substances. The mixture of (1) and (2) optionally may additionally contain conventional additives, such as calcium ions, protease inhibitors, heparin antagonists, substances which promote the infiltration and growth of fibroblasts, such as fibronectin, as well as antibiotics and/or bactericides.

12 Claims, No Drawings

COMPOSITION FOR SEALING AND HEALING WOUNDS

BACKGROUND OF THE INVENTION

1. Field of the Invention

This invention relates to a composition for sealing and healing wounds, comprising a collagen carrier, a fibrinogen component and a thrombin component. The invention is also concerned with a method for the treatment of wounds which comprises administering such a composition to the wound.

2. Description of the Prior Art

It is known that collagen, which is an essential protein of connective tissue, may be used for the treatment of wounds. Collagen may be isolated from, for example, animal hides and sinews by physical and chemical methods, can be modified by such methods, and can be applied to a wound as a sheet, web or foam of collagen as disclosed in United Kingdom Pat. No. 1,205,609.

Moreover, it is known that local stoppage of bleeding, and tissue bonding, may be achieved with blood clotting factors, such as fibrinogen, thrombin and blood clotting factor XIII.

The use of a combination of fibrinogen and collagen to stop bleeding in heart surgery has been described in Wiener Medizinische Wochenschrift 7, 86 to 89 (1976). Admittedly, the use of this combination is time-consuming and expensive in material: freeze-dried human fibrinogen is warmed to 37° C., applied to a collagen web and there caused to clot by addition of an aqueous solution of thrombin and an aqueous solution of factor XIII, after which the collagen is pressed, with the face carrying the fibrin thus formed, onto the bleeding spot. However, it is difficult to find the right point in time for transferring this material onto the wound. If it is transferred too early, the clotting factors run into areas where they are not desired, for example, into blood vessels, whilst if the material is transferred too late, adequate conglutination no longer takes place. In order to be able to react to unexpected hemorrhaging during surgery, it is necessary at all times to have ready a sufficiently large amount of fibrinimpregnated collagen, which is then often not used and must be thrown away.

The material for healing wounds which is described in United Kingdom patent application No. 2,023,614 A and which comprises blood coagulation factor XIII and thrombin fixed per se does not solve this problem, since the material does not contain the fibrinogen also needed for blood coagulation, so that the material is unsuitable for use in, for example, consumptive coagulopathy.

SUMMARY OF THE INVENTION

Surprisingly, it has now been found that it is possible to provide a composition which contains, alongside one another, all the constituents required for blood clotting, which constituents however only react with one another when the composition is used, so that this composition may be stored in a ready-to-use state for a lengthy period. This is possible if the factors required for blood clotting are applied to a collagen carrier in the presence of a medium consisting at least predominantly of an organic solvent, in which case the constituents adhere surprisingly well to the collagen carrier even though fibrin formation has not yet started to a significant extent, if at all.

Accordingly, the present invention provides a composition for sealing and healing wounds comprising collagen and substances which cause blood clotting. The said composition comprises a collagen carrier which is coated on one face or all faces with a mixture of (1) a fibrinogen component containing fibrinogen, factor XIII-containing fibrinogen or a mixture thereof, and (2) a thrombin component, containing thrombin, substances which liberate thrombin in the presence of body fluid, or a mixture of such substances.

The said mixture of (1) and (2) additionally may contain conventional additives, such as calcium ions, protease inhibitors, heparin antagonists, substances, such as fibronectin, which promote the infiltration and growth of fibroblasts, as well as anti-infection medicaments.

To prepare the composition according to the invention, various types of collagen may be used, such as natural collagen or chemically modified collagen, for example, crosslinked collagen, esterified collagen or collagen having modified amino groups.

The collagen carrier may be used in the form of a foam, web or film, collagen foam being particularly preferred.

The fibrinogen component employed may be animal or human fibrinogen, advantageously in an amount of 0.05 to 20 mg/cm$^2$, the range from 0.5 to 5 mg/cm$^2$ being particularly preferred. The fibrinogen may be highly purified or may contain small amounts of clotting factor XIII or may be enriched in clotting factor XIII. Usually, fibrinogen containing 0.5 to 20 units/cm$^2$, preferably 1 to 10 units/cm$^2$, of clotting factor XIII is employed. Clotting factor XIII can also be added separately. The fibrinogen may be employed in a crystalline or amorphous form or as a lyophilizate.

The thrombin component may be of animal or human origin and advantageously may be employed in an amount of 1 $\mu$g to 5 mg/cm$^2$, the range from 50 $\mu$g to 1 mg/cm$^2$ being preferred. It is also possible to employ a combination of factors which liberate thrombin, examples of such factors being prothrombin and clotting factor Xa.

In addition to the clotting factors, conventional substances which influence the process of blood clotting and the healing of the wound may be applied to the collagen carrier. It is particularly advantageous to apply, to the collagen, protease inhibitors, for example aprotinin (1 to 1,000 units/cm$^2$) as well as heparin antagonists, for example protamine chloride (0.01 to 5 mg/cm$^2$), or factors which promote the infiltration and growth of fibroblasts and thereby speed up the healing of the wound, for example fibronectin. Equally, calcium ions, for example as calcium chloride, may be used, in an amount of 2 nmoles to 2 $\mu$moles/cm$^2$.

The composition prepared by the process of the invention also may contain anti-infection medicaments, such as bactericides.

To mark the coated side of the composition according to the invention, it is also possible to add a suitable dye, for example hemin, to the substances to be applied.

The essential object of the invention is that fibrinogen particles and thrombin particles or thrombin-liberating particles are present alongside one another on a collagen carrier, without reacting with one another. This can be achieved by adding an organic solvent to fibrinogen particles and thrombin particles or thrombin-liberating particles in the form of crystals or lyophilizates in an amorphous form, after which a suspension is formed by thorough mixing, for example in a high-speed mixer, with or without comminution of large crystals. This formation of a suspension can be carried out separately for both clotting factors, or in a single step. The other factors influencing clotting and wound healing, ions or medicaments can also be suspended or dissolved in the solvent employed. Thereafter, the suspension is applied, by brushing, spraying or dipping, to one or all faces of the collagen carrier, and the solvent is allowed to evaporate at room temperature or with refrigeration, under atmospheric pressure or under a vacuum. The fibrinogen particles and thrombin particles remain adhering to the collagen surface.

A large number of organic solvents can be used for suspending the clotting factors. The solvents, which may contain small amounts of water, should be sufficiently volatile and should not inactivate the clotting factors. Examples of such solvents or suspending media are lower straight-chain or branched $C_1$-$C_5$-alcohols, especially n-propanol, isopropanol, n-butanol, isobutanol and ethanol, ketones, for example acetone or methyl ethyl ketone, aliphatic or cycloaliphatic ethers, for example dimethyl ether or diethyl ether, tetrahydrofuran or dioxane, esters, for example ethyl acetate, nitriles, such as acetonitrile, and aliphatic halogenated hydrocarbons, for example carbon tetrachloride, methylene chloride and chloroform.

A further possible method of preparing the composition according to the invention is to moisten the collagen carrier with a suitable suspending solvent, which can contain small amounts of water, then to apply the fibrinogen component and thrombin component, as well as the auxiliaries, simultaneously or successively, in a solid form, uniformly to the moistened collagen layer, and to allow the solvent to evaporate. Here again, the particles remain adhering firmly to the surface.

As a modification of the process, it is possible to moisten the collagen carrier with a very small amount of water, which is just sufficient to fix the fibrinogen particles and thrombin particles to the surface of the collagen carrier without significant formation of fibrin.

The collagen carrier may be coated on one or all faces. Coating on one face, namely the side which subsequently faces the wound, is advantageous for closing surgical wounds, since in this way conglutination only occurs on the wound which is to be conglutinated, whilst the formation of adhesions between the internal wound and the tissue opposite the wound is prevented. If, on the other hand, the composition prepared by the process of the invention is used to seal and heal a cavity, an appropriately shaped piece of collagen foam may be dipped into the suspension of the clotting factors, so that it becomes coated on all faces.

Compared to the previously known combination of aqueous fibrin conglutinant and collagen, the composition according to the invention offers substantial advantages:

Since the fibrinogen component and thrombin component have been applied to the collagen carrier with the aid of an organic solvent, that is to say substantially in the absence of water, they dissolve, and form fibrin, only when serum-like fluid or blood reaches them. Accordingly, fibrin formation takes place at exactly the right time, and in the right place. Even if the collagen carrier is moistened with a very small amount of water and then treated with the solid fibrinogen particles and thrombin particles, no significant formation of fibrin occurs, since the water only serves as a binder between the collagen carrier and the individual particles of the clotting factors.

The handling of the composition according to the invention is very simple. It may be employed dry, therefore does not stick to surgical gloves and surgical instruments, and has an advantageous, elastic moldable consistency. Conglutination occurs only on the wound. Since the fibrin only forms in the collagen carrier, heterologous clotting factors, that is to say not of human origin, can also be employed. This has the particular advantage that the danger of transmission of viral hepatitis can be eliminated.

The storage of the composition according to the invention is also simple. It is stored at refrigerator temperature or room temperature, under sterile conditions, with exclusion of moisture, for example by being sealed in a film pouch.

The composition may be used for all types of wound treatment and wound healing. In particular, it is useful for sealing and conglutinating of internal and external wounds, for securing sutures, and for healing of large-surfaced wounds or wound cavities. It is also particularly suitable for use in large or small bone cavities, of surgical or traumatic origin, in which the stoppage of bleeding is often a great problem, for example after dental extractions, otological surgery or fractures.

The following Examples illustrate the invention.

EXAMPLE 1

1,000 mg. of factor XIII-containing fibrinogen (from cattle), 25 mg. of thrombin (from cattle), 5 mg. of $CaCl_2 \times 2H_2O$, 250,000 units of aprotinin and 10 mg. of protamine (for example as the chloride), in a narrow, tall cooled vessel, are mixed with sufficient cooled ethanol that the substances are covered with liquid. The mixture is then homogenized for 30 seconds by means of an Ultra-Turrax apparatus. The suspension is applied to 500 cm$^2$ of collagen foam by means of a spraying apparatus. The ethanol is allowed to evaporate. The particles remain adhering to the surface of the collagen foam.

EXAMPLE 2

1,000 mg. of factor XIII-containing fibrinogen (from cattle), in a narrow, tall cooled vessel, is mixed with sufficient cooled n-propanol that the substance is covered with liquid. The mixture is then homogenized for 60 seconds by means of an Ultra-Turrax apparatus. 50 mg. of thrombin (from cattle), in a narrow, tall vessel, is mixed with sufficient n-propanol that the substance is covered with liquid. The mixture is then homogenized for 10 seconds by means of an Ultra-Turrax apparatus.

The two suspensions are combined and applied to 500 cm$^2$ of a collagen film by means of a spray apparatus. The n-propanol is evaporated off in vacuo. The fibrinogen particles and thrombin particles remain adhering to the collagen surface.

EXAMPLE 3

1,500 mg. of factor XIII-containing fibrinogen (from cattle), 50 mg. of thrombin (from cattle) and 10 mg. of protamine (as the chloride), in a narrow, tall cooled vessel, are mixed with sufficient cooled carbon tetrachloride that the substances are covered with liquid. The mixture is then homogenized for 30 seconds by means of an Ultra-Turrax apparatus. The suspension is applied to 500 cm$^2$ of collagen web by means of a spray apparatus. The carbon tetrachloride is allowed to evaporate. The particles of fibrinogen, thrombin and protamine chloride remain adhering to the surface of the collagen web.

EXAMPLE 4

500 cm$^2$ of collagen foam is sprayed with ethyl acetate until the surface is just moistened. A mixture of the following substances, which have been ground in solid form, is then uniformly distributed over the surface: 1,000 mg. of factor XIII-containing fibrinogen (from cattle), 25 mg. of thrombin (from cattle), 5 mg. of CaCl$_2 \times$2H$_2$O, 250,000 units of aprotinin and 10 mg. of protamine (as the chloride). The ethyl acetate is allowed to evaporate. The particles remain adhering to the surface of the collagen foam.

EXAMPLE 5

1,000 mg. of human fibrinogen containing factor XIII, 30 mg, of human thrombin and 10 mg. of protamine (as the chloride), in a narrow, tall cooled vessel, are mixed with sufficient n-butanol, at 0°–4° C., that the substances are covered with liquid. The mixture is then homogenized for 30 seconds by means of an Ultra-Turrax apparatus. The suspension is applied to 500 cm$^2$ of collagen foam by means of a spraying apparatus. The n-butanol is evaporated off in vacuo. The particles remain adhering to the surface of the collagen foam.

EXAMPLE 6

500 mg. of factor XIII-containing fibrinogen (from cattle), 25 mg. of thrombin (from cattle) and 10 mg. of protamine (as the chloride), in a narrow, tall cooled vessel, are mixed with sufficient ethanol, at 0°–4° C., that the substances are just covered with liquid. The mixture is then homogenized for 30 seconds. Pieces of collagen foam, cut into a conical shape and suitable for plugging dental extraction wounds are dipped in this suspension. The ethanol is allowed to evaporate. The particles remain adhering to the collagen surface.

EXAMPLE 7

500 mg. of fibrinogen (from cattle), 25 mg. of thrombin (from cattle), 1,000 units of factor XIII and 5 mg. of protamine (as the chloride) are mixed, whilst being cooled, with sufficient acetonitrile that the substances are covered with liquid. After homogenization, the suspension is introduced into a vessel having an adjustable exit slot, in the manner of a thin-layer coating machine, and is applied uniformly to 500 cm$^2$ of collagen foam, after which the solvent is allowed to evaporate. The particles applied remain adhering to the surface.

EXAMPLE 8

500 cm$^2$ of collagen foam are sprayed with water by means of a spray apparatus, so as to provide 1 mg of water per cm$^2$. The water is immediately absorbed by the surface of the collagen foam, without a change in the macro-structure of the collagen. 500 mg. of fibrinogen (from cattle), 20 mg. of thrombin (from cattle), 200,000 units/cm$^2$ of aprotinin and 5 mg. of protamine (as the chloride) are applied, as fine particles, to the surface, which has been rendered tacky by the water. After brief storage exposed to the air, the collagen surface loses its tacky consistency. The applied particles remain adhering to the surface.

We claim:

1. A process for the preparation of a composition for sealing and healing wounds which comprises adding a mixture of (1) a fibrinogen component containing fibrinogen, factor XIII-containing fibrinogen or a mixture thereof, and (2) a thrombin component containing thrombin, a substance which liberates thrombin in the presence of body fluid, or a mixture of such substances, to an organic solvent, in the absence of water, homogenizing the resulting slurry to form a homogeneous suspension of the mixture in the solvent, applying the said suspenion to one or more surfaces of a collagen carrier and evaporating the organic solvent, whereby particles of the said mixture remain adhering to the surface or surfaces of the collagen.

2. A process according to claim 1, in which the mixture of (1) and (2) also includes one or more conventional additives selected from the group consisting of calcium ions, protease inhibitors, heparin antagonists, substances which promote the infiltration and growth of fibroblasts and anti-infection medicaments.

3. A process according to claim 1, in which the organic solvent is a straight-chain or branched C$_1$-C$_5$ alkanol, an aliphatic halogenated hydrocarbon, an ester, a nitrile, a ketone or an aliphatic or cycloaliphatic ether.

4. A composition for sealing and healing wounds prepared by the process according to claim 1 and comprising a collagen carrier which is coated on one face or all faces with a mixture of (1) a fibrinogen component containing fibrinogen, factor XIII-containing fibrinogen or a mixture thereof, and (2) a thrombin component, containing thrombin, a substance which liberates thrombin in the presence of body fluid, or a mixture of such substances.

5. A composition according to claim 4, in which the mixture of (1) and (2) also includes one or more conventional additives selected from the group consisting of calcium ions, protease inhibitors, heparin antagonists, substances which promote the infiltration and growth of fibroblasts and anti-infection medicaments.

6. A composition according to claim 4 or 5, wherein the collagen carrier is a collagen foam.

7. A composition according to claim 4 or 5, wherein the amount of the fibrinogen component is 0.05 to 20 mg/cm$^2$.

8. A composition according to claim 7, wherein the amount of the fibrinogen component is 0.5 to 5 mg/cm$^2$.

9. A composition according to claim 4 or 5, wherein the amount of the thrombin component is 1 $\mu$g to 5 mg/cm$^2$.

10. A composition according to claim 9, wherein the amount of the thrombin component is 50 $\mu$g to 1 mg/cm$^2$.

11. A composition according to claim 5, wherein the conventional additive which promotes the infiltration and growth of fibroblasts is fibronectin.

12. A method for the treatment of wounds, which comprises administering to the wound a composition prepared by the process according to claim 10 and comprising a collagen carrier which is coated on one face or all faces with a mixture of (1) a fibrinogen component containing fibrinogen, factor XIII-containing fibrinogen or a mixture thereof, and (2) a thrombin component, containing thrombin, a substance which liberates thrombin in the presence of body fluid, or a mixture of such substances.

* * * * *